US006692771B2

(12) United States Patent
Pather et al.

(10) Patent No.: US 6,692,771 B2
(45) Date of Patent: Feb. 17, 2004

(54) EMULSIONS AS SOLID DOSAGE FORMS FOR ORAL ADMINISTRATION

(75) Inventors: S. Indiran Pather, Plymouth, MN (US); Sangeeta V. Gupte, Waukegan, IL (US); Rajendra K. Khankari, Maple Grove, MN (US); John Hontz, Plymouth, MN (US); Ramya Kumbale, Morris Plains, NJ (US)

(73) Assignee: CIMA Labs Inc., Eden Prairie, MN (US)

( * ) Notice: Subject to any disclaimer, the term of this patent is extended or adjusted under 35 U.S.C. 154(b) by 0 days.

(21) Appl. No.: 09/792,659

(22) Filed: Feb. 23, 2001

(65) Prior Publication Data

US 2002/0160049 A1 Oct. 31, 2002

(51) Int. Cl.[7] .............................. A61K 9/16; A61K 9/20; A61K 9/48; A61K 47/04

(52) U.S. Cl. ........................ 424/498; 424/465; 424/458; 514/770

(58) Field of Search ................................. 424/464, 470, 424/474, 489, 490, 458, 469, 498; 514/770

(56) References Cited

U.S. PATENT DOCUMENTS

| | | | |
|---|---|---|---|
| 4,353,806 A | 10/1982 | Canter et al. | 252/8.55 D |
| 4,360,061 A | 11/1982 | Canter et al. | 166/274 |
| 4,751,241 A | 6/1988 | Motoyama et al. | 514/532 |
| 5,178,878 A | 1/1993 | Wehling et al. | 424/466 |
| 5,206,219 A | 4/1993 | Desai | 514/3 |
| 5,393,527 A | 2/1995 | Malick et al. | 435/7.1 |
| 5,435,936 A | 7/1995 | Broze | 252/162 |
| 5,444,041 A | 8/1995 | Owen et al. | 514/2 |

(List continued on next page.)

OTHER PUBLICATIONS

Guillemet, F. and Piculell, L., "Interactions in Aqueous Mixtures of Hydrophobically Modified Polyelectrolyte and Oppositely Charged Surfactant. Mixed Micelle Formation and Associative Phase Separation", J. Phys. Chem., 99:9201–09 (1995).

Nelson, Ph.D., E., "Part VXII. Physicochemical and Pharmaceutic Properties of Drugs that Influence the Results of Clinical Trials", Clin. Pharmacol. Ther., 3(5):673–81 (1962).

Ebert, W. R., "Soft Elastic Gelatin Capsules: A Unique Dosage Form", Pharm. Tech., 1(5):44–50 (1977).

Spieras, et al., "Powdered Solution Technology: Principles and Mechanisms", J. Pharm. Res., 9(10):1351–58 (1992).

Sheth, A. and Jarowski, C.I., "Use of Powdered Solutions To Improve The Dissolution Rate of Polythiazide Tablets", Drug Dev. Ind. Pharm., 16(5):769–77 (1990).

Jonathan D. Eichman, "Mechanastic Studies On Effervescent–Induced Permeability Enhancement" Dissertation, University of Wisconsin–Madison (1997).

*Microemulsion technology in the reformulation of cyclosporine: the reason behind the pharmacokinetic properties of Neoral*, Ritschel, Clin. Transp. 1996: 10: 364–73.

*A comparison of two quality assessment methods for emulsions*, Pather et al., J. Pharm. &Biomedical Analysis, 1995: 13: 1283–89.

*Primary Examiner*—Edward J. Webman
(74) *Attorney, Agent, or Firm*—Lerner, David, Littenberg, Krumholz & Mentlik, LLP

(57) ABSTRACT

Novel emulsion compositions which improve the rate and/or extent of absorption of drugs are disclosed. The novel emulsion compositions of the present invention include drug-containing emulsions adsorbed onto solid particles which may be further formulated into solid dosage forms, methods of preparing such emulsion compositions and their uses thereof. The emulsion compositions and their dosage forms improve the drug-load and the bioavailability of a wide range of drugs including drugs that are known or suspected of having poor bioavailability by the utilization of several different mechanisms.

28 Claims, 1 Drawing Sheet

U.S. PATENT DOCUMENTS

| | | | |
|---|---|---|---|
| 5,580,735 A | 12/1996 | Malick et al. | 435/6 |
| 5,593,843 A | 1/1997 | Malick et al. | 435/7.1 |
| 5,620,903 A | 4/1997 | Malick et al. | 436/533 |
| 5,633,226 A | 5/1997 | Owen et al. | 514/2 |
| 5,635,357 A | 6/1997 | Malick et al. | 435/7.1 |
| 5,646,109 A | 7/1997 | Owen et al. | 514/2 |
| 5,656,289 A | 8/1997 | Cho et al. | |
| 5,688,697 A | 11/1997 | Malick et al. | 436/518 |
| 5,688,761 A | 11/1997 | Owen et al. | 514/2 |
| 5,800,834 A | 9/1998 | Spireas et al. | 424/451 |
| 5,997,905 A | 12/1999 | McTeigue et al. | 424/490 |
| 6,228,400 B1 * | 5/2001 | Lee et al. | 424/451 |
| 6,280,770 B1 | 8/2001 | Pather et al. | |
| 6,379,700 B2 | 4/2002 | Joachim et al. | |

* cited by examiner

EMULSIONS AS SOLID DOSAGE FORMS FOR ORAL ADMINISTRATION

FIELD OF THE INVENTION

The present invention relates to the field of emulsion compositions and to pharmaceutical dosage forms and the methods of preparing the same.

BACKGROUND OF THE INVENTION

Certain drugs present significant problems in balancing the desire for a convenient oral dosing format and the necessary bioavailability. With some drugs, absorption of an orally administered dose could be as little as 30%, or less. Such poorly absorbed drugs often display large inter- and intra-subject variability in bioavailability. See Aungst, B. J., J. Pharm. Sci., 82:979–987, 1993. Specific examples of such drugs, having the average bioavailability given in parentheses, include methyldopa (25%) with a range of 8% to 62%; and nalbuphine (approximately 17%) with a range of 6% to 40%.

The absorption rate of most drugs depends on two factors: (1) the dissolution of the drug in physiological fluids and (2) the absorption process itself, i.e., the process by which a drug in solution enters the cells at the absorption site and, finally enters the general circulation. Many drugs are absorbed by passive diffusion, i.e., a spontaneous migration of drug molecules from a region of high concentration to a region of low concentration. Other drugs are absorbed by active transportation which involves the expenditure of energy by the body. Some drugs are absorbed by the processes of pynocytosis or endocytosis which involve the engulfing of solid particles and the incorporation of such particles into the cellular contents. However, with these few exceptions, for solid orally administered drugs, absorbed actively or passively, dissolution of the drug is the first step in the absorption process.

To compensate for the poor absorption displayed by many drugs, a pharmaceutical formulation may utilize or take advantage of one or more mechanisms to increase the rate and/or the extent to which the administered drug is absorbed. While there are a vast number of such mechanisms, they may be grouped into the following broad categories: (1) techniques that increase rate of absorption by enhancing the rate or extent of dissolution; (2) techniques that increase rate of absorption by facilitating the absorption process that would have occurred naturally; and (3) techniques that increase rate of absorption by inducing an absorption mechanism that would not naturally have occurred or which would have occurred to an insignificant extent in the absence of any special absorption-enhancing mechanism. Incorporation of surfactants to increase the rate of dissolution of a slowly-dissolving drug is an example of a technique which takes advantage of the first mechanism, and incorporation of a chemical substance that opens tight junctions in order to increase the rate of absorption of a drug that would normally have been absorbed slowly through the paracellular route is an example of the use of the second technique. On the other hand, incorporation of a drug within oil droplets for the purpose of using the lymphatic system in the absorption of the drug (where this would not, otherwise, have occurred) is an example of a third technique using the third mechanism.

Emulsions have also been used for delivering drugs. The emulsions are generally delivered only in the form of soft or hard gelatin capsules, or as a liquid dispensed directly into the patient's mouth. However, gelatin capsule shells contain water which can migrate into water-in-oil ("w/o") emulsions. This can change the relative proportions of the different phases of the emulsion and/or cause the gelatin shell to become dry and susceptible to cracking. Alternatively, a w/o emulsion can lose water to the gelatin shell, again changing the proportions of the different emulsion phases or causing the shell to swell and become soft. The latter effect makes it difficult for a patient or care-giver to handle the capsule. Moreover, surfactants and co-surfactants within the emulsions, often used as emulsifying agents, can react with the capsule shell. Oil-in-water ("o/w") emulsions generally cannot be incorporated in such capsules because the water in the external phase will dissolve the capsule shell. In addition, gelatin capsules which contain liquids present handling problems to both the patient and the manufacturers. Capsule leakage is a common problem and sophisticated detection systems are sometimes employed to monitor such leakage. Upon physical handling by the patient, the capsule may also soften or leak. With prolonged storage at temperatures and humidity levels that are not as closely controlled as the environment in a pharmaceutical factory, the capsule may also swell, shrink or leak.

More recently, powdered solution technology has been proposed as a technique for the delivery of water-insoluble drugs. See Spireas et al., "Powdered Solution Technology: Principles and Mechanisms, Pharm. Research, Vol. 9, No. 10 (1992) and Sheth, A. and Jarowski, C. I., "Use Of Powdered Solutions To Improve The Dissolution Rate Of Polythiazide Tablets," Drug Development and Industrial Pharmacy, 16(5), 769–777 (1990). The concept of powdered solutions involves converting drug solutions or liquid drugs into a dry, nonadherent, free-flowing compressible powder by admixing the liquid drugs or drug solutions with a selected carrier. Although the dosage form is a solid, the drug is held in a solubilized liquid state, which enhances diffusion directly into cells. Alternately, it improves the wetting properties of the drug and, therefore, enhances dissolution.

Unfortunately, the application of powder solution technology has been limited.

While the technology offers certain promise in enhancing the drug-delivery performance, in practice, the resulting admixture powders generally have undesirable properties, such as poor and erratic flowability and compressibility. The disclosure of the co-pending commonly assigned U.S. patent application Ser. No. 09/374,393 and the corresponding international application PCT/US99/18552 published under Pub. No. WO009093A1 is incorporated herein by reference.

SUMMARY OF THE INVENTION

One aspect of the invention provides an emulsion composition in the form of a free-flowing, compressible powder, which includes an admixture of a drug-containing emulsion and a solid particle adsorbent; wherein the emulsion is adsorbed on the solid particle adsorbent and forms a free-flowing, compressible powder. The drug-containing emulsion remains stable in the composition. Preferably, the drug containing emulsion has a viscosity of between 1 cps and 400,000 cps, preferably between 400 cps and 200,000 cps and more preferably between 5,000 cps and 150,000 cps. The drug-containing emulsion may include between 2% and 50% active drug ingredient, preferably between 5% and 40% and more preferably between 10% and 30%.

The emulsion compositions according to this aspect of the present invention do not limit the types of dosage form and can be administered to a subject in any pharmaceutically acceptable dosage. For example, the emulsion compositions may be administered as dosage forms, such as tablets; granules, pellets or other multiparticulates; capsules that can contain the drug in the form of mini-tablets, beads, or a powder; suppositories; or as a powder of the emulsion composition itself, either packaged in a multidose container or as individual doses.

In another aspect, the invention also provides an emulsion composition in the form of a free-flowing, compressible powder. The emulsion composition is an admixture of a drug-containing self-emulsifying drug delivery system and solid particle adsorbents. The drug-containing self-emulsifying drug delivery system is a mixture of oil, emulsifying agent and active drug ingredient and the mixture is adsorbed onto the solid particle adsorbent when blended with the adsorbent. Compositions according to this aspect of the invention can be made into dosage forms similar to those discussed above.

The emulsion compositions discussed above may be prepared by adsorbing a drug-containing emulsion onto a particulate solid material so as to provide the emulsion composition in the form of a powder. The powder can then be made into other solid dosage forms by combination with additional excipients using conventional processing. The dosage form of the emulsion composition can also be directly packaged and administered without further processing.

Administration of drugs in the above-mentioned dosage forms offers significant advantages over the previously available methods of administration.

In certain preferred embodiments of the present invention, absorption of the drug is facilitated by the administration of the drug-containing-emulsion compositions. Although the present invention is not limited by any theories of operation, it is believed that upon the disintegration of a dosage form which contains the emulsion compositions of the invention, emulsion droplets are distributed through a large volume of the gastrointestinal fluids. This prevents the formation of large agglomerates of individual emulsion droplets in localized regions. When the droplets come into contact with the surface tissues of the body cavity, this widespread distribution aids in the absorption of the drug over a large surface area.

In another aspect of the invention, emulsion compositions and dosage forms containing them are used to enhance the bioavailability of poorly absorbed drugs that are oil soluble. This is accomplished by administering these drugs as oil-in-water (o/w) emulsions. The oil soluble drug is distributed as droplets of an oily solution which is then used to make an emulsion where water is the continuous phase. The emulsion is adsorbed onto a powder and formulated into a dosage form. When ingested, oil droplets may be absorbed by the tissue together with the incorporated drugs. The oil droplets may also be positioned adjacent to the absorbing surface so that the drug in such oil droplets can diffuse into the cell membrane. In addition, due to the fact that there are many such droplets, as noted above, the surface area of the absorbing tissues with which the droplets make contact is large, thus facilitating absorption. Furthermore, since in vivo agglomeration is retarded, absorption can be facilitated.

The emulsion compositions of the present invention may be also used to promote absorption though the M-cells of Peyer's patches. These M-cells are involved in the absorption of very small solid particles of the order of 10 micrometers. Since the individual solid support particles described in this disclosure only partially release the emulsion droplets following administration of the dosage forms to mammals, there are free emulsion droplets as well as emulsion droplets attached to solid particles at the absorption site. In a preferred embodiment, the droplet-solid support complex is sufficiently small to be absorbed via the M-cells.

The emulsion globules of the emulsion compositions of the invention may also promote absorption though the lymphatic system. Such absorption relates especially to the free (detached) emulsion droplets but may also relate to the droplets adsorbed and remain adsorbed onto the carrier support. Drugs absorbed via the lymphatic system pass directly from this system into the general blood circulation and hence avoid the first pass effect.

In addition, emulsion compositions in accordance with the invention may facilitate administration of drugs that are subject to metabolic breakdown or degradation in the gastrointestinal tract, such as, for example, peptides, proteins, oilgonucleotides and other biological molecules. Such drugs may be protected within, for example, the oil droplets in o/w emulsions. As used herein, the word "protection" refers to the protective effect that reduces the rate and/or extent of the drug molecule degradation in vivo. The emulsion components of the present invention make it difficult for enzymes and other chemical substances to react with such drug molecules when they are encased in oil and/or the emulsifying agent(s).

The emulsions of the present invention are administered in the form of solid particles which may be further formulated into solid dosage forms. The drug-containing emulsions are adsorbed onto a solid particulate (i.e., powder). Although the drug is in a solid form, it is maintained as an emulsion, or in the case of self-emulsifying drug delivery systems ("SEDDS"), in a state readily converted to an emulsion in vivo. Preferably, these formulations enhance dissolution into aqueous fluids and/or absorption into the body. Although the present invention is not limited by any theories of operation, it is believed that the SEDDS is adsorbed on the adsorbent particles in the form of oil globules or form a film. When these SEDDS-containing adsorbent particles are administered and in contact with the body fluid, they form an emulsion composition.

SEDDS consists of all components of the emulsion except the water i.e. it consists of the oil phase, emulsifying agents, anti-oxidants, preservatives and other optional excipients. Upon mixing with the stomach contents, an emulsion is formed. It can be distinguished from an emulsion in that it is a one-phase system: it does not have droplets of one liquid distributed throughout a second liquid. It can be distinguished from an oil (that may be adsorbed on a solid support) by the fact that the oil does not contain emulsifying agents and, in general, will not form an emulsion upon mixing with the stomach contents.

In addition to enhancing the saturation concentration (saturation solubility) of the pharmaceutical substance, the pharmaceutical compositions and solid dosage forms of the present invention also increase the substance surface area of the drug-containing emulsion. The adsorbent particles increase the area available for interaction with gastrointestinal fluids and/or with the site of absorption to thereby promote absorption of the drug.

In a further preferred aspect of the present invention, an emulsion composition is in a solid dosage form that is convenient and easy to handle. The solid dosage forms represent a robust, stable dosage form. Moreover, the solid dosage form that is more patient-acceptable and thus provides potential for better patient compliance. There are many patients who do not like to take capsules and for whom an alternate dosage form, such as a tablet, is preferable. In addition, the present invention provides a form for the oral administration of peptides which are generally administered by injection, which is unpleasant for the patient.

DETAILED DESCRIPTION OF THE PREFERRED EMBODIMENTS

Figure 1:
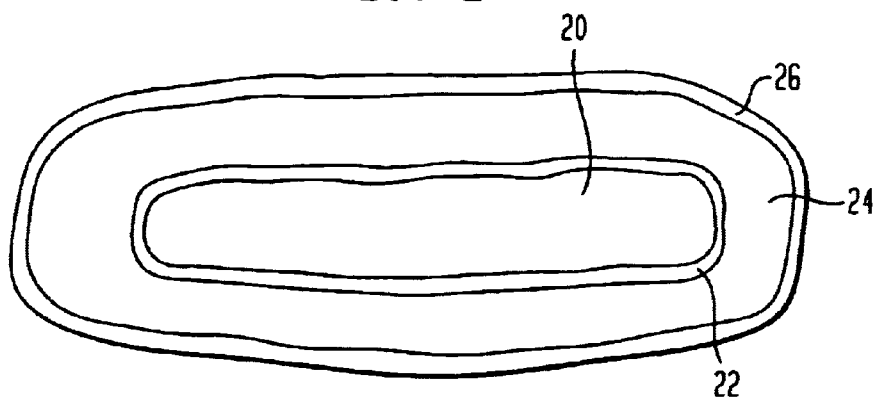
FIG. 1 is an enlarged top plan view of a tablet according to one embodiment of the invention.

An emulsion composition according to one embodiment of the invention is provided in the form of a free-flowing, compressible powder, comprising: an admixture of a drug-containing emulsion and a solid particle adsorbent. The emulsion is adsorbed on the solid particle adsorbent and preferably forms a free-flowing, compressible powder, wherein the drug-containing emulsion is stable in the emulsion composition.

An emulsion, as referenced to herein, is a system of two immiscible liquid phases. One of the two phases (the internal phase) is distributed as droplets/globules throughout the second phase (the external, or continuous phase). As used herein, emulsions include oil-in-water (o/w) emulsions, in which a less polar liquid commonly referred to as an oil is in the internal phase; and water-in-oil (w/o) emulsions, in which an aqueous or other relatively polar liquid is in the internal phase. The present invention also includes the use of self-emulsifying drug delivery systems (SEDDS) which consist of all the components of an o/w emulsion (oil, emulsifying agents, antioxidant, preservative and the like) except water. Generally, an emulsion composition containing SEDDS can be prepared by adsorbing SEDDS to adsorbent powder. After administration of the emulsion compositions containing SEDDS, an emulsion forms in vivo upon admixing with the body fluids. Generally, emulsions can also be classified as fine emulsions with globule diameters of less than 5 μm and coarse emulsion with globule diameters greater than 5 μm.

The oil phase in the emulsion can be any nontoxic oil, which includes, but is not limited to mono-, di- and triglycerides, fatty acids and their esters, ethers and esters of propylene glycol or other polyols. The fatty acids and esters (used as such or where they form part of a glyceride) may be short chain, medium chain or long chain. As used herein, medium chain represents a hydrocarbon chain of $C_8$ to $C_{12}$ and short chain is a hydrocarbon chain of less than $C_8$ and long chain means a hydrocarbon chain of more than $C_{12}$.

The water phase in the emulsion can be water, aqueous solutions, alcohols, alcohol solutions, and the like.

The oil phase may be of vegetable or animal origin. The oil phase may also be synthetic or semisynthetic, or substances which are nontoxic to the subject. The oils include, but are not limited to, natural oils, such as cottonseed oil, soybean oil, sunflower oil; canola oil; CAPTEX® (various grades Propylene Glycol Esters such as Propylene Glycol didecanoate; and Glycerol esters such as Glyceryl tricaprylate/caprate); MIGLYOL® (Caprylic/capric acid triglycerides; or Caprylic/capric/linoleic acid triglycerides; or Caprylic/capric/succinic acid triglycerides; or Propylene glycol diester of caprylic/capric acid and admixtures with other agents); CAPMUL® (available in different grades, e.g. Capmul MCM. It is mainly mono- and di-esters of glycerol and of propylene glycol, such as glyceryl monooleate and propylene glycol monocaprilate. Another grade consists of polyethylene glycol glyceryl monostearate.)

The formation of emulsions also requires emulsifiers or emulsifying agents. As used herein, any nontoxic emulsifying agent may be used in the present emulsion. This includes, but are not limited to, various grades of the following commercial products: MYVACET® (distilled acetylated monoglyceride emulsifers); ARLACEL® (mainly sorbitan esters); TWEEN®(polyoxyethylene sorbitan esters); CENTROPHASE®(fluid lecithins); CREMOPHOR® (polyoxyl castor oil derivatives; or macrogol ethers; or macrogol esters); LABRAFAC® (caprylic/capric triglyceride); LABRAFIL® (polyoxyethylated glycolysed glycerides); LABRASOL® (mixture of mono-, di- and triglycerides and mono-and di-fatty esters of polyethylene glycol. The predominant fatty acids are $C_8$–$C_{10}$ caprylic/capric acids); MYVEROL®; and TAGAT® (polyethyleneglycol hydrogenated castor oil; or polyethyleneglycol glyceryl esters); lecithin; cholesterol and proteins such as casein. Multiple emulsifying agents can be used to maintain the internal phase distributed as globules throughout the external phase and to retard coalescence of the globules into larger drops. In this way, the two phases can be kept in relative stability for a longer period of time.

In pharmaceutical emulsions used in the present invention, one or both phases is a drug or a solution of one or more drugs. Indeed, either or both the water and the oil phases may contain drugs at the same time and those drugs may be the same or different. Any two immiscible liquids that are non-toxic and compatible with the part of the mammalian body to which they are to be applied, may be used.

In the present invention, oil phase, aqueous phase and emulsifier can be used in a wide range of ratios to make the emulsions. Oil-in-water emulsions generally contain at least 25% of water by weight, preferably between 60% and 98% and more preferably between 70% and 90%. The oil phase in the o/w emulsions is desirably at least 1% of the emulsion by weight, preferably between 5% and 69% and more preferably between 8% and 40%. (The active drug ingredient is included in the weight of the oil phase.) The emulsifier in the emulsions is at least 0.5% by weight, preferably between 2% and 25% and more preferably between 5 and 10%.

Water-in-oil emulsions generally contain at least 25% oil phase by weight of the w/o emulsion, preferably between 40% and 98% and more preferably between 50% and 95%. The water phase in w/o emulsions desirably is at least 1% of the w/o emulsion by weight, preferably between 2% and 55% and more preferably between 5% and 30%. (The active drug ingredient is included in the weight of the water phase.) The emulsifier in w/o emulsion desirably is at least 0.5% of the w/o emulsion by weight, preferably between 2% and 20%, and more preferably between 4 and 10%.

Emulsifying agents or combinations of agents are used for o/w or w/o formulations in accordance with the HLB (hydrophile-lipophile balance) system. w/o emulsions require low HLB emulsifying agents (HLB value approximately 1 to 7) and o/w systems require higher HLB emulsifying agents (HLB value approximately 11 to 18). In general, the type of emulsifying agent used and the relative proportions of oil and water determine whether the emulsion is a w/o or o/w emulsion. This refers to the emulsion upon formation. Some emulsions may invert when added to a large volume of the internal phase. Thus, an emulsion that is prepared as w/o emulsion, upon consumption by the patient may invert to an o/w emulsion in the patient's stomach.

Generally, an emulsion can be prepared by mixing the oil phase, the water phase, the emulsifier, etc in a propeller mixer, a turbine mixer or other high shear mixer and stirring the mixtures vigorously.

The adsorbent is placed in the bowl of a suitable mixer, such as a planetary mixer, and the emulsion is added slowly with mixing. The rate of addition should not be so fast as to form clumps of wet material or, alternately, areas that are much more wet than other areas of powder. If powder clumps or wet portions of power are encountered, the rate of emulsion addition should be reduced or, preferably, temporarily stopped until the wet portion of powder is well distributed throughout the bulk of the powder. The planetary mixer is well suited to this operation since it is equipped with a scraper bar that scrapes material off the sidewalls of the vessel. Overly wet material often accumulates on the sidewalls and would not have mixed well with the bulk powder, except for the action of the scraper bar.

The practice of this invention is, obviously, not limited to the planetary mixer but any mixer that affords uniform mixing of powders with liquids will suffice. Mixers that have dead space should be avoided. A dead space, for purposes of the present discussion, is one in which powder can collect but in which space the powder is not subject to the mixing action of the apparatus. Mixers which have a secondary mixing action, in addition to the primary action, are preferred. The secondary mixer action may be a scraper (as in the planetary mixer) or an intensifier bar or other high shear component. Generally, the mixing action of the mixer should provide an intense mixing zone where high shear of the powder is experienced as well as an additional mixing action which moves all portions of the powder through the intense mixing zone i.e. there should be a three dimensional shuffling of the bulk powder.

The addition of the emulsion to the powder may be accomplished by the operator simply pouring the emulsion into the mixer bowl (containing the powder) from a beaker or measuring cylinder, or by more sophisticated means such as spraying the liquid onto the powder at a controlled rate. A peristaltic pump may be used to add liquid at a controlled rate. The spray nozzle used in conjunction with the peristaltic pump should, preferably, provide a fine spray. A spray head that is used with a fluidized bed coater is ideal. The spray rate should not be so fast, or the droplets so fine, that there is a large amount of spray that does not reach the powder but is dissipated outside the mixing bowl. Such over spray will not be incorporated into the product and this loss should be minimized.

The present invention is applicable to both water-soluble and water-insoluble drugs. The drug may be combined with either the oil phase or the water phase depending on its solubility and other characteristics. A drug dissolved in one phase may partition into the other phase to some extent and this would affect the bioavailability of the drug, in general.

Any active substance (drug) may be used in the emulsion. Liquid drugs, drug solutions, small molecule drugs and nutritional supplements, such as vitamins and minerals, are suitable for use in the present invention.

As used herein, the phrase "small molecule" includes any inorganic chemical molecules, organic chemical molecules having a molecular weight of less than 3,000 daltons.

Preferably, the drug is chosen from one or more of the following categories/groups: abortifacient/interceptive, ace- inhibitor, α-adrenergic agonist, β-adrenergic agonist, α-adrenergic blocker, β-adrenergic blocker, adrenocortical steroid, adrenocortical suppressant, adrenocorticotropic hormone, alcohol deterrent, aldose reductase inhibitor, aldosterone antagonist, 5-alpha reductase inhibitor, anabolic, analeptic, analgesic, androgen, angiotensin converting enzyme inhibitor, angiotensin II receptor antagonist, anorexic, antacid, anthelmintic, antiacne, antiallergic, antialopecia agent, antiamebic, antiandrogen, antianginal, antiarrhythmic, antiarteriosclerotic, antiarthritic/antirheumatic, antiasthmatic, antibacterial, antibacterial adjuncts, antibiotic, anticancer, anticholelithogenic, anticholesteremic, anticholinergic, anticoagulant, anticonvulsant, antidepressant, antidiabetic, antidiarrheal, antidiuretic, antidote, antidyskinetic, antieczematic, antiemetic, antiepileptic, antiestrogen, antifibrotic, antiflatulent, antifungal, antiglaucoma, antigonadotropin, antigout, antihemorrhagic, antihistaminic, antihypercholesterolemic, antihyperlipidemic, antihyperlipoproteinemic, antihyperphosphatemic, antihypertensive, antihyperthyroid, antihypotensive, antihypothyroid, anti-infective, anti-inflammatory, antileprotic, antileukemic, antilipemic, antimalarial, antimanic, antimethemoglobinemic, antimigraine, antimycotic, antinauseant, antineoplastic, antineoplastic adjunct, antineutropenic, antiosteoporotic, antipagetic, antiparkinsonian, antiperistaltic, antipheochromocytoma, antipneumocystis, antiprostatic hypertrophy, antiprotozoal, antipruritic, antipsoriatic, antipsychotic, antipyretic, antirheumatic, antirickettsial, antiseborrheic, antiseptic/disinfectant, antispasmodic, antisyphilitic, antithrombocythemic, antithrombotic, antitubercular, antitumor, antitussive, antiulcerative, antiurolithic, antivenin, antivertigo, antiviral, anxiolytic, aromatase inhibitors, astringent, benzodiazepine antagonist, beta-blocker, bone resorption inhibitor, bradycardic agent, bradykinin antagonist, bronchodilator, calcium channel blocker, calcium regulator, calcium supplement, cancer chemotherapy, capillary protectant, carbonic anhydrase inhibitor, cardiac depressant, cardiotonic, cathartic, CCK antagonist, central stimulant, cerebral vasodilator, chelating agent, cholecystokinin antagonist, cholelitholytic agent, choleretic, cholinergic, cholinesterase inhibitor, cholinesterase reactivator, CNS stimulant, cognition activator, contraceptive, control of intraocular pressure, converting enzyme inhibitor, coronary vasodilator, cytoprotectant, debriding agent, decongestant, depigmentor, dermatitis herpetiformis suppressant, diagnostic aid, digestive aid, diuretic, dopamine receptor agonist, dopamine receptor antagonist, ectoparasiticide, emetic, enkephalinase inhibitor, enzyme, enzyme cofactor, enzyme inducer, estrogen, estrogen antagonist, expectorant, fibrinogen receptor antagonist, gastric and pancreatic secretion stimulant, gastric proton pump inhibitor, gastric secretion inhibitor, gastroprokinetic, glucocorticoid, α-glucosidase inhibitor, gonad-stimulating principle, gout suppressant, growth hormone inhibitor, growth hormone releasing factor, growth stimulant, hematinic, hematopoietic, hemolytic, hemostatic, heparin antagonist, hepatoprotectant, histamine $H_1$-receptor antagonist, histamine $H_2$-receptor antagonist, HIV proteinase inhibitor, HMG CoA reductase inhibitor, hypnotic, hypocholesteremic, hypolipidemic, hopotensive, immunomodulator, immunosuppressant, intropic agent, insulin sensitizer, ion exchange resin, keratolytic, lactation stimulating hormone, laxative/cathartic, leukotriene antagonist, LH-RH agonist, lipotropic, 5-lipoxygenase inhibitor, lupus erythematosus suppressant, major tranquilizer, matrix metalloproteinase inhibitor, mineralocorticoid, minor tranquilizer, miotic, monoamine oxidase inhibitor, mucolytic, muscle relaxant, mydriatic, narcotic analgesic, narcotic antagonist, nasal decongestant, neuroleptic, neuromuscular blocking agent, neuroprotective, nootropic, nsaid, opioid analgesic, oral contraceptive, ovarian hormone, oxytocic, parasympathomimetic, pediculicide, pepsin inhibitor, peripheral vasodilator, peristaltic stimulant, pigmentation agent, plasma volume expander, potassium channel activator/opener, pressor agent, progestogen, prolactin inhibitor, prostaglandin/prostaglandin analog, protease inhibitor, proton pump inhibitor, pulmonary surfactant, 5α-reductase inhibitor, replenishers/supplements, respiratory stimulant, retroviral protease inhibitor, reverse transcriptase inhibitor, scabicide, sclerosing agent, sedative/hypnotic, serenic, serotonin noradrenaline reuptake inhibitor, serotonin receptor agonist, seratonin receptor antagonist, serotonin uptake inhibitor, skeletal muscle relaxant, somatostatin analog, spasmolytic, stool softener, succinylcholine synergist, sympathomimetic, thrombolytic, thromboxane $A_2$-receptor antagonist, thromboxane $A_2$-sythetase inhibitor, thyroid hormone, thyroid inhibitor, thyrotropic hormone, tocolytic, topical protectant, topoisomerase I inhibitor, topoisomerase II inhibitor, tranquilizer, ultraviolet screen, uricosuric, vasodilator, vasopressor, vasoprotectant, vitamin/vitamin source, vulnerary, Wilson's disease treatment, xanthine oxidase inhibitor.

More preferably, the drug is selected from the group consisting of acyclovir; auranofin; bretylium; cytarabine; doxepin; doxorubicin; hydralazine; ketamine; labetalol; mercaptopurine; methyldopa; nalbuphine; nalozone; pentoxifyll; pyridostigmine; terbutaline; verapamil; buserelin; calcitonin; cyclosporin; oxytocin and heparin.

Generally, the drug-containing emulsion contains between 0.5% and 60% active drug ingredient. The active drug ingredient is preferably in the range of between 2% and 50% of the total weight of the drug-containing emulsion (both phases), more preferably between 5% and 40% and most preferably between 10% and 30%. The drug containing emulsion preferably has a viscosity of between 1 cps and 400,000 cps, preferably between 400 cps and 200,000 cps and more preferably between 5,000 cps and 150,000 cps.

The emulsions are also suitable for the administration of active substances that display poor bioavailability, slow absorption or long $t_{max}$. These include drugs that are poorly absorbed, drugs that are degraded during passage through the gastro-intestinal system, such as, for example, proteins, peptides and other biological molecules. In particular, the protection offered to a drug contained within the internal oil phase of an emulsion makes this system particularly suitable for proteins and peptides and other biological molecules.

As used herein, the phrase "biological molecule" includes, but is not limited to polypeptides, DNA molecules, RNA molecules, polysaccharides, and the like.

The emulsion may also contain additional excipients such as preservatives, antioxidants, colors, flavors and fragrants, etc. Non-limiting examples of preservatives include methylparaben, propylparaben, benzoic acid and cetylpyridinium chloride.

Emulsions, including drug-containing emulsions, have different characteristics as compared with, for example, microemulsions. Generally, both emulsions and microemulsions consist of globules of one phase, e.g. water, in another phase, e.g. oil, wherein the emulsion globules have larger diameter than the microemulsion globules. Generally, emulsions have globules with mean diameters (the average diameter of all globules in the emulsion) larger than 0.1 μm or 100 nm, particularly in the range of 0.16 μm to 40 μm, while microemulsions contain globules having diameter of less than 0.1 μm. However, emulsions and microemulsions are not necessarily differentiated by the globule size of the internal phase. Instead, they may differ in one or more of the following defining properties:

microemulsions can form easily with little mixing energy needed and often without heating. They often form spontaneously, i.e. the ingredients in the correct proportions spontaneously form microemulsions once placed in a container. On the other hand, emulsions are thermodynamically unstable and require vigorous stirring with a high-shear mixer and usually need heating to a higher temperature, e.g. 75° C.

The physical appearances of microemulsion and emulsion are different. Microemulsions are transparent (like water) because the globules in microemulsions are too small to refract light. Emulsions are usually white or cream in color.

Microemulsions are thermodynamically stable at room temperature. Once the microemulsion is formed, it can be stable for many years in a sealed container and under normal storage condition. Emulsions have a tendency for the individual globules of the interior phase to coalesce (grow together) into larger and larger drops over time. Therefore, emulsion are generally stable for a relatively shorter period of time in bulk solution if it is left undisturbed, as the emulsion breaks or cracks to form completely separate phases, when compared to an otherwise identical microemulsion. S. Indiran Pather et al., J. Pharm. & Biomed. Anal. 13 (1995) 1283–1289. It is believed that when an emulsion is adsorbed onto an adsorbent, it remains stable for a longer period of time than the same emulsion in bulk solution. Without being limited by any theory of operation, it is believed that upon adsorption, dispersion of the emulsion on the adsorbent retards coalescence of the interior phase globules with one another.

The addition of specific proportions of each of the components and even their order of mixing plays a role in the formation of emulsions, which also differentiates emulsions from microemulsions. Such knowledge and information on the formation of emulsions is usually known by those skilled in the art and may be gleaned from standard pharmaceutical texts such as Physical Pharmacy by Alfred Martin, Lea and Febiger, 4th Ed. (1993).

In a preferred embodiment of the invention, the drug-containing emulsion comprises emulsion globules having mean or modal diameters of greater than 100 nm, preferably between 120 nm and 70 μm, and more preferably between 160 nm and 10 μm. The drug containing emulsion of the emulsion composition is preferably stable for at least one year when left in a closed container at 25° C. and can be an oil-in-water emulsion, a water-in-oil emulsion, or a self-emulsifying drug delivery system, which converts to an emulsion in vivo.

In the present invention, the drug-containing emulsions are adsorbed/absorbed onto adsorbents/absorbents (these two terms are collectively referred to as "adsorbent" or "adsorbents"). Adsorbents should be nontoxic and should include fine particles having diameters in the range of 25 nm to 50 μm, preferably in the range of 50 nm to 30 μm and more preferably in the range of 100 nm to 20 μm. Suitable adsorbents include, but are not limited to, clays such as kaolin, bentonite, hectorite and colloidal magnesium aluminum silicate; silicon dioxide (CAB-O-SIL® or AEROSIL®); magnesium trisilicate; aluminum hydroxide; magnesium hydroxide, magnesium oxide or talc. More preferably the adsorbent is silicon dioxide.

A further aspect of the invention also provides an emulsion composition in the form of a free-flowing, compressible powder, comprising: an admixture of a drug-containing self-emulsifying drug delivery system and a solid particle adsorbent; preferably, the drug-containing self-emulsifying drug delivery system is adsorbed onto said solid particle adsorbent and forms a free-flowing, compressible powder. Direct compression tableting excipients can also be added to the free-flowing compressible powder to improve its compressibility.

The proportion of emulsion to solid support preferably varies from about 1:20 to about 10:1. More preferably, the proportion of emulsion to solid support is about 1:5 to about 2:1.

The drug-containing emulsion composition is prepared by adsorbing the drug-containing emulsion onto an adsorbent. Generally, the adsorbent is placed in a mixer and then the drug-containing emulsion having a predetermined ratio to the adsorbent, is poured into the mixer at constant stirring to achieve uniform adsorption of the emulsion to the adsorbent.

The resulting product of adsorbing drug-containing emulsions to adsorbents should preferably be a free-flowing, compressible powder. Once the emulsion is adsorbed onto the solid support, ideally, the powder should resemble a completely dry powder (as far as observation with the eye can discern) and the powder is preferably free flowing as defined in the angle of repose test described below. This is more easily achieved with an o/w emulsion, partly due to the fact that the water in the external phase partially evaporates during the incorporation process. There is an equilibrium amount of water that is retained on the particles of the solid support. When adsorbing a w/o emulsion, there is a greater tendency for the powder to appear slightly "wet". Nevertheless, even with a w/o emulsion the powder should not be cohesive. The proportion of emulsion to solid support is an important factor in determining the extent to which the powder remains free flowing and dry. However, with the proportions of solid support to emulsion referred to earlier, it is possible to obtain a noncohesive mixture. For the manufacture of compressed tablets, this mixture is then combined with the other tableting components to obtain a compressible blend. This compressible blend should be free flowing.

The extent to which the powder blend is free flowing is estimated by conducting an angle of repose test as detailed in a standard pharmaceutical text such as "The Theory And Practice Of Industrial Pharmacy" by Lachman, Lieberman and Kanig (Lea and Febiger, publishers), hereby incorporated by reference herein. The static angle of repose test is preferred. When such a test is performed, the final powder blend should have, preferably, an angle of repose less than 42 degrees, and preferably less than 40 degrees.

In order for the mixture of adsorbent and emulsion to form a free-flowing powder that can easily be compressed, the proportion of emulsion is kept relatively low in the emulsion-adsorbent composition. Consequently, the drug-load in the drug-containing emulsion becomes a significant factor in formulating a stable, high bioavailable and high drug-load composition.

Surprisingly it has been discovered that one can incorporate a wide range of drug load into such free flowing, compressible powders while increasing the stability of the pharmaceutical emulsion, as the emulsions of the present invention can be formed from a wide range of weight ratios of water, oil and the emulsifying agent and can be adsorbed onto a solid particulate adsorbent to form a free flowing, compressible powder. The final drug dosage form can contain between 0.1 mg and 1,000 mg of active drug ingredient/tablet (of e.g. 2.4 grams), preferably between 5 mg and 500 mg, more preferably between 10 mg and 200 mg and the most preferably between 15 mg and 100 mg.

Coating can also be applied to the individual particles of the emulsion composition powder; to agglomerates, granules or other larger particles incorporating multiple particles of the composition or to solid dosage forms or portions of dosage forms. The term "multiparticulate" as used herein means a composition in the form of multiple particles. Each particle may be an individual particle of the powder composition or may be an agglomerate, granule, or other larger particle incorporating or formed from multiple particles of the powder composition. The coating can also be used in conjunction with an effervescence to cause the effervescence to occur at specific areas of the gastrointestinal tract. Non-limiting examples of coatings used in the present invention include: cellulose derivatives including cellulose acetate phthalate (CAP); shellac and certain materials sold under the trademark EUDRAGIT® (various grades are available with differing properties and may be used in specific combinations). Hydroxypropylmethyl cellulose phthalate in a grade that dissolves at pH 5 is the preferred coating material for enteric coating purposes, for example when the coating must resist the acidic environment of the stomach but must dissolve in the duodenum.

Coatings may preferably be done in a fluidized bed coater or a coating pan. While either type may be used for both tablets, powders and multiparticulates, the fluidized bed coater is preferred for multiparticulates while the pan coater is preferred for tablets. In the fluidized bed coater process, the multiparticulates are first prewarmed within the apparatus by blowing warmed air through the container. If the active drug ingredient is a temperature-sensitive material, such as peptide, low temperatures are used so that the potency of the drug is not affected. The volume of fluidizing air penetrating the bed per hour is chosen such that the material to be coated is fluidized and flowing in a gentle pattern. The effect of the atomizing air should, additionally, be taken into account. The coating solution is sprayed on at a rate that will wet the material to be coated within the spray zone, have time to flow around the particulates and then be dried within the drying zone of the apparatus. If the liquid spray rate is too slow (or the temperature of the drying inlet air is too high, or the inlet air is too rapid), the liquid droplets dry before they touch the particles, resulting in the addition of spray dried material to the multiparticulates. When the spray rate is too fast (or the inlet air is introduced too slowly, or its temperature is too low) the liquid does not dry fast enough. The material remains wet, causing agglomeration of the material. At the correct conditions, the coating material neither dries too quickly nor allows prolonged wetting of the material to be coated. These operating conditions can be adequately chosen by one ordinarily skilled in the art.

This invention further provides a solid dosage form for the administration of a therapeutically effective amount of a drug, comprising: (1) an emulsion composition in the form of a free-flowing, compressible powder which comprises an admixture of a drug-containing emulsion and a solid particle adsorbent; wherein the emulsion is adsorbed on the solid particle adsorbent, and (2) optionally excipients, including fillers, binders, disintegrants, viscosity modifiers, lubricants, colors, flavors and the like.

In one embodiment of the invention, the solid dosage form is a tablet, a pellet, a minitablet, or a capsule for oral administration, or a tablet for intra-oral administration, or a tablet for vaginal administration, a suppository for vaginal administration, a suppository for rectal administration. A tablet for oral administration may be of the type which is adapted to release constituents of the tablet within the mouth, so that the released constituents can be swallowed with or without the consumption of water or other liquid to assist swallowing. Powders can also be dosage forms in and of themselves. The solid dosage form can further comprise a bioadhesive.

In another embodiment of the invention, the solid dosage form further comprises an enteric coating maintained over the dosage form or over the portion of the dosage form which includes the emulsion composition. The enteric coating prevents the release of the drug-containing emulsion until a time at which the dosage form reaches a target area following oral administration. Any coating that can accomplish this is contemplated. However, the enteric coating preferably may be selected from materials of the group consisting of EUDRAGIT S100 (a methacrylic acid copolymer produced by Rohm Pharma Gmbh of Germany), sugar, gelatin, hydroxypropyl cellulose or hydroxypropylmethyl cellulose phthalate, cellulose acetate phthalate, polyvinylacetate phthalate, methacrylic acid copolymer, shellac, hydroxypropylmethylcellulose succinate, cellulose acetate trimellitate, and their mixtures thereof.

In a further embodiment of the invention, the dosage forms contain materials that aid in releasing the drug in a specific section of the gastrointestinal tract to promote site-specific delivery. The chosen site for drug release is usually the most efficiently absorbing part of the gastrointestinal tract for the drug in question, or one that offers some other therapeutic advantage. The added materials promote site-specific delivery by various mechanisms and this invention is not limited to any one such mechanism. For example, the material may be metabolized by enzymes present in a specific part of the gastrointestinal tract, thus releasing the drug in that section. The materials used to promote site-specific absorption may be used as coatings and/or matrix materials and include, for example, sugars, polysaccharides, starches, polymers, and the like.

The solid dosage form can further comprise excipients, such as, at least one effervescent agent and/or at least one disintegration agent; wherein the disintegration agent causes rapid dispersion and breaking up of the dosage form following oral administration. A pH adjusting substance may also be used as an excipient.

This invention also provides a method for preparing an emulsion composition, comprising the steps of: preparing a drug-containing emulsion and converting the drug-containing emulsion into a free-flowing, compressible powder by admixing the drug-containing emulsion with a solid particle adsorbent. Stable emulsion compositions prepared by the method are also contemplated.

This invention also provides a method for preparing a solid dosage form for the vaginal or rectal administration of a therapeutically effective amount of a drug, comprising the steps of: preparing a drug-containing emulsion; admixing said drug-containing emulsion with a solid particle adsorbent to form a free-flowing compressible powder; incorporating said free-flowing, compressible powder, with the optional addition of one or more excipients into a tablet, suppository or other solid dosage form.

Various ingredients and/or techniques can be used in combination with the dosage forms of the present invention to further enhance bioavailability, including, the administration of and agents which aid in the site specific delivery of the drug-containing emulsions, agents which increase the rate of dissolution. This may be achieved through the structural and fluidity changes to the biological membranes induced by the chosen surfactants. The selected enhancement technique is preferably related to the route of drug absorption, i.e., paracellular or transcellular. These techniques include, but are not limited to, the use of additional chemical penetration enhancers; mucoadhesive materials; effervescent couples; ion pairing or complexation agents; and the use of lipid and/or surfactant drug carriers.

A bioadhesive polymer may be included in the dosage form to increase the contact time between the dosage form and the mucosa of the most efficiently adsorbing section of the gastrointestinal tract. See Jonathan D. Eichman, "Mechanastic Studies On Effervescent-Induced Permeability Enhancement," University of Wisconsin-Madison (1997), hereby incorporated by reference herein. Nonlimiting examples of known bioadhesives used in the present invention include: Carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

Disintegration agents may also be employed to aid in dispersion of the drug in the gastrointestinal tract. Disintegration agents include any pharmaceutically acceptable effervescent agent. In addition to the effervescence-producing disintegration agents, a dosage form according to the present invention may include suitable noneffervescent disintegration agents. Nonlimiting examples of disintegration agents include: microcrystalline cellulose, croscarmelose sodium, crospovidone, starches and modified starches.

Apart from the effervescent material within the tablet, some additional effervescent components or, alternatively, only sodium bicarbonate (or other alkaline substance) may be present in the coating around the dosage form.

The purpose of the latter effervescent/alkaline material is to react within the stomach contents and promote faster stomach emptying.

Additionally, pH-adjusting substances, as described in U.S. patent application Ser. Nos. 09/302,105 and 09/327,814, hereby incorporated by reference herein, may also be used to increase absorption of a drug. The various components may be present in layers within the dosage form or specialized shapes and geometric arrangements may be employed. Dosage forms according to the invention can include drugs in addition to those carried in the emulsion-containing composition.

A tablet in accordance with one embodiment of the present invention (FIG. 1) includes a core 20, a barrier coating 22 which is, in turn, covered by an effervescent layer 24. An enteric coating 26 covers the effervescent layer 24. Core 20 includes an emulsion composition of the present invention. When the tablet reaches the small intestine, the enteric coat 26 dissolves, exposing the effervescent layer. Reaction of this layer with the aqueous fluid of the gastrointestinal tract releases carbon dioxide. This aids absorption in several ways including, for example, the thinning of the mucus layer, thus bringing the tablet into closer contact with the absorptive surface (mucosa). Barrier coating 22 prevents the water within the adsorbed emulsion from reacting with the effervescent material 24. With some w/o adsorbed emulsions, it may be possible to omit the barrier coating without causing extensive deterioration of the tablet.

This is due to the fact that the effervescent material is protected from the water of the adsorbed emulsion by the fact that the tiny water droplets of the emulsion are completely surrounded by oil and do not react readily with the effervescent components. With the dissolution of the enteric coating 22 and barrier coating 22 (if used), the core of the tablet is exposed, facilitating disintegration of the core, release of the emulsion droplets from the adsorbent and subsequent drug release from the emulsion.

Figure 2A:
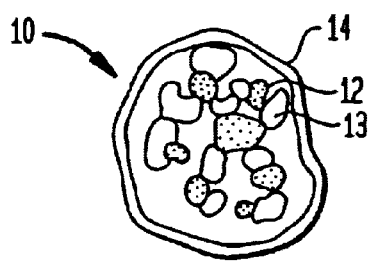
FIG. 2A is a cross-section view of a tablet according to another embodiment of the invention.
Figure 2B:
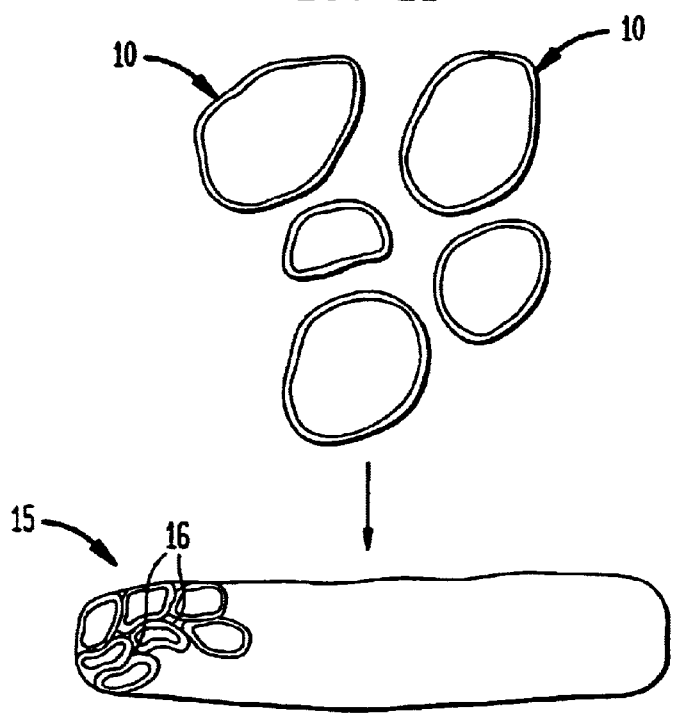
FIG. 2B is a schematic diagram for the preparation of a soft tablet.

A second design, which is illustrated in FIG. 2, includes agglomerates 10, each of which includes agglomerate of multiple particles 12 of adsorbent, having adsorbed emulsion 13 seen in a schematic representation in FIG. 2A. The agglomerates are coated with an enteric material 14. The coated agglomerates are then compressed together into a relatively soft tablet 15, with fillers, flavors, sweeteners, disintegrants and other excipients added. The compressed tablet may include some interstitial spaces 16, which can be filled with a filler. Such a tablet, which may be much larger than a conventional tablet, is allowed to disintegrate within the oral cavity. Disintegration, which usually occurs within 2 minutes, and more preferably within 1 minute, releases the enteric-coated agglomerates which are swallowed. This enables absorption to occur at a site distal to the oral cavity. Absorption usually occurs in the duodenum. However, the preparation can contain other components which promote absorption at other sites such as, but not limited to, the colon. This tablet may contain effervescence to aid disintegration and palatability or may include enteric-coated effervescent granules which promote absorption in the duodenum or other targeted site.

Particles may be manufactured by granulation (wet or dry process), layering techniques, extrusion and spheronization or other pellet manufacturing methods. Dry granulation may be achieved through slugging or chilsonation of a powder mix (including adsorbed emulsion) that has the appearance of a dry powder. Layering may be done in a fluid bed apparatus or coating pan. The fine powder with the adsorbed emulsion (having the appearance of a dry powder) is layered onto the starting material or cores. Aqueous or non-aqueous binders are used to aid the adherence of the added material onto the cores. The choice of binder is dictated, in part, by the nature of the emulsion and the drug being utilized in a particular preparation. The binder should be tested for its effect on drug stability. Only the binders which do not negatively affect drug stability in the emulsion will be used. Layering is preferably done in a fluidized bed coater. In this apparatus, the bed of material remains wet for a very short time and, hence, it is often possible to use a binder that may, at first sight, appear incompatible. In addition to the fine particle-adsorbed emulsion, other materials may be layered onto the starting material. These include, without limitation, the drug or additional amounts of the drug, penetration enhancers, and other excipients. Nonlimiting examples of the starting material or cores are nonpareils (sucrose) or microcrystalline cellulose seeds. The size of the multiparticulates is preferably up to about 3 mm. Coating of the dosage forms or the multiparticulates may be accomplished in a fluid bed coater or by other coating techniques. The multiparticulates may be packed into capsules.

Where a wet process, such as wet granulation or extrusion and spheronization is used, the emulsion is, preferably, used as the liquid phase or granulating fluid. More preferably, o/w emulsions are used as the liquid phase in the wet process since this type of emulsion may be diluted with water to give the correct consistency for processing with the solid components and, furthermore, partial drying of the formed particulates will result in a product that has a dry appearance. Inclusion in the external aqueous phase of water-miscible, non-toxic, volatile organic solvents such as, for example, isopropyl alcohol, or ethyl alcohol may be advantageous in facilitating the partial evaporation of the external phase of the emulsion from the formed particulates.

A variation of this design is one in which the material does not contain an enteric coat, but is retained in the oral cavity where the drug is released for absorption by the oral mucosa. When the latter design is utilized, the tablet may contain additional penetration enhancers, mucoadhesives or other agents to facilitate absorption in the oral cavity.

Tablets can be manufactured by wet granulation, dry granulation, direct compression or any other tablet manufacturing technique. Orally disintegrating tablets may be relatively soft and are preferably made by direct compression in accordance with the disclosures in U.S. Pat. No. 5,178,878, which are hereby incorporated by reference herein. For peptides and other biological molecule, low compression forces are preferable because these substances are sensitive to compression forces. With such compounds, the conformation of the compound and the biological activity can change with the higher compression forces that are conventionally used in tablet manufacture.

The tablet may be a layered tablet consisting of a layer of the active ingredients, set forth above, within layers of diverse compositions. Alternatively, the tablet may be a simple tablet of uniform composition. In accordance with the present invention, the tablet size is preferably up to about ¾ inch. The tablet hardness is preferably between about 5 Newton ("N") and about 50 N and more preferably between about 15N and 35N for an uncoated tablet. Tablets that are intended to be coated, for example with an enteric coat, are preferable slightly harder, having hardness values of 20N to 70N and more preferably from 25N to SON. These values relate to the uncoated cores and, as expected, the hardness values of the tablets increase due to the addition of the coating layer.

The tablet may be one that is intended for vaginal administration in which case it, preferably, contains fine particle powders as the filler and other excipients to reduce the potential for physical irritation or abrasion. In addition the tablet is of a special shape to facilitate insertion into the vagina. Non-limiting examples of such shapes include oval and diamond-shaped. The insertion of the tablet may be facilitated by the use of a special applicator device well known in the industry for this purpose.

Tablets containing the emulsion can be coated with an enteric material. This is preferably done in a coating pan. Many of the modern, perforated pans have features which make for more efficient coating. As an example, the Hicoater (Vector Corporation, Iowa) may be used. The tablets within the pan are preheated and the pan is rotated at a rate that allows gentle tumbling of the tablets. Many of the comments regarding the actual process (such as rate of wetting of the material) made for the fluidized bed coater, apply to the pan coater as well. The coating solution should be non-aqueous when effervescent material is incorporated within the preparation and the effervescence preferably separated from the emulsion by a coating.

Precoating materials may also be used in the present invention. Nonlimiting examples of precoating materials include cellulose derivatives such as methylcellulose, hydroxypropyl cellulose, hydroxypropyl methylcellulose or combinations and certain materials sold under the trademark EUDRAGIT® (various grades which may be combined).

Excipients, such as fillers can be used in connection with the present invention to facilitate tableting. Nonlimiting examples of fillers include: mannitol, dextrose, lactose, sucrose, and calcium carbonate. For a tablet intended to disintegrate in the oral cavity, the mass of the tablet should, preferably, not exceed 2.5 g. If an effervescent agent is included, the effervescence level in the tablet is preferably between about 5% and 65% by weight based on the weight of the finished tablet.

The emulsion adsorbed onto a fine particle adsorbent may be incorporated into a suppository formed, for example, by molding. In this technique, the free-flowing powder is mixed with the molten suppository base(s) and poured into a mold and allowed to set by cooling to ambient temperature. Suitable suppository bases include, but are not limited to, cocoa butter, polyethylene glycols, polyvinyl pyrrolidone, gelatin, gelatin/glycerin combinations, esterified fatty acids, polyoxyethylene sorbitans and polyoxyethylene sorbitan fatty acid esters. Various proprietary bases which may contain mixtures of different components are also available. Examples of proprietary bases are those sold under the trade names Imhausen, Witepsol and Gelucire. Various grades of each of these are available for specific applications. Mixtures of various bases may also be utilized in order to obtain a suppository with the required properties.

Various additives may be incorporated into the suppositories of the present invention including surfactants and absorption enhancers such as medium chain ($C_8$ to $C_{12}$) fatty acids and fatty acid esters including mono-, di-, and triesters of glycerol. Other shaping methods for forming the suppositories including cold molding and compression may also be used.

It is preferable that the hydrophilic/hydrophobic nature of the suppository base be different from the external phase of the emulsion i.e. where an o/w emulsion is used, the suppository base should be a fatty (hydrophobic) base such as cocoa butter; in the case of a w/o emulsion, the suppository base should be hydrophilic such as, for example, a gelatin/glycerin base. This helps to maintain the stability of the emulsion by preventing the formation of a miscible mixture between the external phase of the emulsion and the suppository base.

Various publications are cited throughout this application. These publications are hereby incorporated by reference.

The invention will further be described by reference to the following examples. These examples are provided for the purpose of illustration only, and are not intended to be limiting unless otherwise specified.

EXAMPLE 1

Preparation of Oil-In-Water Emulsion

| Ingredients | Amount |
| --- | --- |
| Liquid paraffin | 200 g |
| Lovostatin | 79.523 g |
| Chloroform | 1.2 g |
| Benzoic acid solution* | 10 g |
| Methylcellulose 20 | 7 g |
| Water | to 500 g |

*Benzoic acid solution consists of 5 g benzoic acid, 75 mL propylene glycol and water to 100 mL. The emulsion contains about 15.9% of the drug, Lovostatin.

Procedures of Preparing Emulsions:

The drug was dispersed in the liquid paraffin with gentle heat and stirring. The aqueous phase was prepared separately as follows. The methylcellulose was dispersed in 100 mL of hot water. An additional 120 mL of cold water was added to this and stirred to form a homogeneous gel. The chloroform was added to the benzoic acid solution slowly with stirring and this mixture was added to the aqueous phase and stirred.

The oil phase was added to the water phase and stirred with a propeller stirrer. The emulsion was made up to 500 mL by the addition of water. The formed emulsion was passed several times through a homogenizer until the globules of oil, as determined by observation using a microscope, were less than 20 μm in diameter. The technique for evaluating the sizes of emulsion globules was described in publications such as "A comparison of two quality assessment methods for emulsions" by S. I. Pather, S. H. Neau and S. Pather, Journal of Pharmaceutical and Biomedical Analysis 13 (1995) 1283–1289 which is hereby incorporated herein by reference.

EXAMPLE 2

Adsorption of Emulsion onto Silicon Dioxide

| Ingredients | Amount in g |
| --- | --- |
| Emulsion (from example 1) | 500 |
| Colloidal Silicon dioxide | 1500 |
| Total | 2000 |

Procedures of adsorbing emulsion onto silicon dioxide: Place colloidal silicon dioxide powder into the bowl of a planetary mixer and add the emulsion slowly with continuous mixing to obtain a powder that was dry to the touch.

EXAMPLE 3

Formula for Tablets Using Oil-In-Water Emulsion

| Ingredients | mg/tablet | % w/w |
| --- | --- | --- |
| Emulsion/Silicon dioxide (3:1) (from example 2) | 251.5 | 50.3 |
| Prosolv 90 | 153.0 | 30.6 |
| Spray dried lactose | 55.0 | 11.0 |
| Crospovidone | 33.0 | 6.6 |
| Magnesium Stearate | 7.5 | 1.5 |
| Total | 500.0 | 100.0 |

Procedures for formulating tablets using oil-in-water emulsion: Emulsion/Silicon dioxide, Prosolv 90 (silicified microcrystalline cellulose), Spray dried lactose, and Crospovidone was weighed and screened into a blender and blended for 30 minutes. Then, Magnesium Stearate was weighed and added to the blender and blended a further 5 minutes. The blend was discharged and compressed into tablets using ½ inch punches.

EXAMPLE 4

Coating Solution Formula

| Ingredients | g/batch |
| --- | --- |
| Hydroxypropyl methylcellulose phthalate (HP 55S) | 372 |
| Triethyl Citrate | 28 |
| Ethanol | 1800 |
| Acetone | 1800 |
| Total | 4000 |

Procedure: The coating solution was prepared by adding HP 55S to ethanol and acetone in a large beaker and stirring vigorously. The mixture was stirred until the HP 55S had gone into solution completely. Triethyl Citrate was then added and stirred further to obtain the final solution used to coat tablets produced in example 3. The coating was carried out in a coating pan to limit loss of material from the tablets due to friability. The airflow during the coating process was maintained at 30 CMH (cubic meters/hr) and spray rate was 9.5 g/min. The pan speed was maintained at 20 rpm. The inlet air temperature was maintained between 42 and 45 C and coating was continued until a weight gain of 15% was obtained. Each final tablet contains about 10 mg of Lovostatin.

EXAMPLE 5

Preparation of Water-In-Oil Emulsion Formulation

| Ingredients | g/batch |
| --- | --- |
| Polyethylene glycol castor oil | 300 |
| Mineral oil | 3,700 |
| Propylene glycol | 1,000 |
| Water-soluble drug | 500 |
| Water | 4,500 |

The water-soluble drug in example 5 is calcitonin, or an oligonucleotide, such as those having 8 to 12 base pairs. Mix together the oil phase, i.e. polyethylene glycol castor oil and mineral oil and heat to 75° C. Then mix together the water phase ingredients, i.e. water, water-soluble drug and propylene glycol and heat to 75° C. In preparing the water phase, the water-soluble drug is preferably dissolved in propylene glycol first and then this drug-propylene glycol solution is added to water. Add the water phase to the oil phase and mix thoroughly under vigorous stirring to form w/o emulsion formulation. This w/o emulsion formulation is then adsorbed onto silicon dioxide and the emulsion/adsorbent is incorporated into a tablet as described in this application.

Drugs that would benefit from such treatment are water-soluble but poorly absorbed drugs. The heat stability of the drug must be taken into account when formulating in this fashion. If the drug is dissolved in hot water and the water phase is rapidly mixed with oil phase and then allowed to cool, it may be possible to prepare the emulsion without undue degradation of the drug. An overage of the drug may be incorporated to accommodate the amount lost during heating and mixing.

EXAMPLE 6

High Drug Loading in Emulsion Formulation

One hundred grams of Vitamin E Acetate (α-tocopherol acetate) are emulsified with suitable emulsifying agents to form approximately 200 g of an emulsion formulation per batch of 1,000 tablets. This emulsion formulation contains about fifty percent of Vitamin E Acetate. This emulsion formulation is adsorbed onto approximately 600 g of silicon dioxide. The silicon dioxide with adsorbed emulsion formulation is incorporated into 1,000 orally disintegrating tablets which has a total mass of approximately 2,400 g, using suitable direct compression ingredients. The emulsion has a pleasant taste which is not "oily." The fact that the liquid is adsorbed further contributes to the pleasant organoleptic experience of the person consuming this preparation. Additional flavoring and sweetening agents may also be incorporated into the product.

These tablets are convenient to take, especially for those patients who do not like to take capsules. In addition, it may offer enhanced absorption by the patient's body because the emulsified droplets of vitamin E acetate are adsorbed onto fine particles which may then become distributed over a large area of the gastrointestinal tract. The larger surface area available for absorption allows for more efficient absorption.

EXAMPLE 7

Medium Drug Loading

| Ingredients | Amount |
| --- | --- |
| Liquid paraffin | 200 g |
| Chloramphenicol | 200 g |
| Chloroform | 1.2 g |
| Benzoic acid solution (as in example 1)* | 10 g |
| Methylcellulose 20 | 7 g |
| Water | to 500 g |

The emulsion is prepared in the same way as in example 1. The final drug content in the emulsion is about 40%.

EXAMPLE 8

Low Drug Loading

| Ingredients | Amount |
| --- | --- |
| Liquid paraffin | 120 g |
| Dexamethasone | 10 g |
| Chloroform | 1.2 g |
| Benzoic acid solution (as in example 1)* | 10 g |
| Methylcellulose 20 | 4 g |
| Water | to 500 g |

The product is prepared in a similar fashion to the lovostatin tablets (example 1) but each tablet will contain 0.5 mg dexamethasone. The emulsion contains about 2% of drug, dexamethasone. The 500 g of emulsion is again adsorbed onto about 1,500 g of silicon dioxide. Since the emulsion contains sufficient drug for 20,000 tablets, only 100 mg of the emulsion/solid support mixture need be used per tablet. The mass of the tablet is 500 mg. The lower loading of emulsion/solid support per tablet makes it easier to produce a suitable tablet. Obviously if slightly more than 1,500 g of silicon dioxide is used in the adsorption step, the amount of mixture per tablet would be slightly more.

EXAMPLE 9

Preparation of SEDDS

| Ingredients | Amount |
| --- | --- |
| Liquid paraffin | 200 g |
| Lovostatin | 80 g |
| Chloroform | 1 g |
| $Al_2O_3$ | 400 g |

The oil phase containing Lovostatin is prepared in the same way as in example 1. The oil phase is then adsorbed onto the $Al_2O_3$ particles in the form of oil droplets or oil film.

EXAMPLE 10

Suppository

Fifty milligrams of testosterone enantate is dissolved in 0.25 ml sesame oil (per suppository). Using suitable emulsifying agents the oil is converted into approximately 0.5 ml of an o/w emulsion. This is adsorbed onto approximately 0.8 g of silicon dioxide which is incorporated into a hydrophobic suppository base, such as hydrogenated triglyceride. Suppositories each weighing approximately 2 g are molded from this mixture. Upon administration, the suppository melts and the emulsion on the solid support is dispersed in the rectal fluids. This aids in absorption, while this mode of administration eliminates painful injections.

As Used Herein, Suppositories Include, but are not Limited to the Following:Suppository Bases

| | |
| --- | --- |
| Adeps Solidus | Triglycerides of saturated fatty acids with mono- and diglycerides |
| Cebes Pharma 16 | Modified palm kernel oil |
| Cotomar | Partially hydrogenated cottonseed oil |
| S-70-XX95, X70-XXA | Rearranged hydrogenated vegetable oils |
| Hydrokote | Higher melting fractions of coconut and palm kernel oil; upon request, may contain 0.25% lecithin |
| Idropostal (water soluble) | Condensation product of polyethylene oxide |
| Kaomel | Fractionated Hydrogenated Triglycerides |
| Massa Estarinum | Mixture of tri-, di-, and monoglycerides of saturated fatty acids $CH_{11}H_{23}COOH$ to $C_{17}H_{35}COOH$ |
| Massa Mf 13 (fat soluble) | Mixture of di- and triglycerides of saturated fatty acids |
| Neosuppostal-N | Hydrogenated triglyceride with fatty alcohols and emulsifiers |
| Paramount B | Hydrogenated interesterified vegetable oils |
| Satina ITT | Fractionated hydrogenated triglycerides |
| Suppocire | Eutectic mixtures of mono-, di-, and triglycerides derived from natural vegetable oils |
| Novata | Mixture of tri-, di-, and monoglycerides of saturated fatty acids |
| Suppostal | Hydrogenated triglyceride with fatty alcohols and emulsifiers |
| Wecobee W | Triglycerides |
| Wecobee R | Higher melting fractions of coconut oil and palm kernel oil (may contain 0.25% lecithin) |
| Witepsol | Triglyceride of saturated vegetable fatty acids with monoglycerides (formerly marketed as "Imhausen bases") |
| Tween 61 | Polyethylene glycol sorbitan monostearate |

Versatility of Emulsions Compared to Microemulsions

Examples 7 to 8 above illustrate the versatility of emulsions in delivering drugs in comparison to microemulsions. To prepare a suitable emulsion for the low dose drug, a formulator can take the emulsion for the high dose (which required a high volume of oil for dispersion of the larger amount of drug) and modify it easily for the low dose drug. Since less oil is needed in low dosage drug, less emulsifying agent is added. These changes, i.e. from high dosage drug to low dosage drug, decrease the viscosity of the emulsion and make it easier for the formulator to handle. This interchangeability between high dosage drug and low dosage drug formula can easily be made using emulsion by one of ordinary skill in the art. In fact, an emulsion formula can be altered much more "at will".

By contrast, microemulsions have a fixed formulation and thus, can only be varied within a narrow range. Usually, the volume of the internal phase (oil in this example) cannot be varied by much. In order to know how much the microemulsion formula can be varied and yet remain a microemulsion, the formulator would have to prepare several formulations and plot triangular phase diagrams to obtain the zones in which a microemulsion exists. The triangular phase diagram has to be determined for each particular system and it is a time consuming task.

What is claimed is:

1. An emulsion composition in the form of a free-flowing, compressible powder, comprising:
   an admixture of a drug-containing emulsion and a solid particle adsorbent; wherein said drug-containing emulsion has a viscosity of between about 400 cps and about 200,000 cps, emulsion globules having diameters of between about 120 nm and about 70 μm, and wherein said emulsion is adsorbed on said solid particle adsorbent.

2. The emulsion composition of claim 1, wherein the drug-containing emulsion comprises between 2% and 50% drug.

3. The emulsion composition of claim 1, wherein drug-containing emulsion is stable for at least one year.

4. The emulsion composition of claim 1, wherein said drug-containing emulsion is an oil-in-water emulsion.

5. The emulsion composition of claim 1 wherein said drug-containing emulsion is a water-in-oil emulsion.

6. The emulsion composition of claim 1, wherein said drug-containing emulsion is a self-emulsifying drug delivery system which converts to an emulsion in vivo.

7. The emulsion composition of claim 1, wherein said solid particle adsorbent is selected from the group consisting of kaolin, bentonite, hectorite, colloidal magnesium aluminum silicate, silicon dioxide, magnesium trisilicate, aluminum hydroxide, magnesium hydroxide, magnesium oxide and talc.

8. The composition of claim 1, wherein the compressibility of the free-flowing compressible powder is further improved by the addition of direct compression tableting excipients.

9. The emulsion composition of claim 1, wherein the drug contained in the emulsion is a drug that displays poor bioavailability in the gastrointestinal tract of a mammal, when said drug is administered in a conventional dosage form that does not contain any penetration enhancer or other mechanism to enhance drug absorption.

10. The emulsion composition of claim 1, wherein said drug-containing emulsion includes a drug selected from the group consisting of peptides, proteins, oligonucleotides and other biological molecules.

11. The emulsion composition of claim 1, wherein said drug-containing emulsion includes a nutritional supplement.

12. The emulsion composition of claim 1, wherein said drug-containing emulsion includes a drug selected from the group consisting of acyclovir; auranofin; bretylium; cytarabine; doxepin; doxorubicin; hydralazine; ketamine; labetalol; mercaptopurine; methyldopa; nalbuphine; nalozone; pentoxifylline; pryridostigmine; terbutaline; verapamil; buserelin; calcitonin; cyclosporin; heparin; and oxytocin.

13. A solid dosage form for the administration of a therapeutically effective amount of a drug, comprising:
the emulsion composition of claim 1 and optionally a filler.

14. The solid dosage form of claim 13, wherein said solid dosage form is a tablet for oral administration.

15. The solid dosage form of claim 13, wherein said solid dosage form is a tablet including a plurality of particles wherein at least some of said particles contain said emulsion composition.

16. The solid dosage form of claim 13, wherein said solid dosage form is a capsule for oral administration.

17. The solid dosage form of claim 13, wherein said solid dosage form is a tablet for intra-oral administration, wherein said tablet is allowed to disintegrate in the oral cavity of a mammal, wherein the constituents of the tablet can be swallowed without the consumption of water or other liquid to assist swallowing.

18. The solid dosage form of claim 13, wherein said solid dosage form further comprises a bioadhesive.

19. The solid dosage form of claim 13, wherein said solid dosage form is a tablet for vaginal administration.

20. The solid dosage form of claim 13, wherein said sold dosage form is a suppository for vaginal administration.

21. The solid dosage form of claim 13, wherein said solid dosage form is a suppository for rectal administration.

22. The solid dosage form of claim 13, wherein said solid dosage form further comprises an enteric coating maintained over said dosage form; wherein said enteric coating prevents the release of said drug-containing emulsion until a time at which said dosage form reaches a target area following oral administration.

23. The solid dosage form of claim 22, wherein the enteric coating is selected from materials of the group consisting of a methacrylic acid copolymer, sugar, gelatin, hydroxypropyl cellulose or hydroxypropylmethyl cellulose phthalate, cellulose acetate phthalate, polyvinylacetate phthalate, methacrylic acid copolymer, shellac, hydroxypropylmethylcellulose succinate, cellulose acetate trimellitate, and their mixtures thereof.

24. The solid dosage form of claim 13, wherein said solid dosage form further comprises at least one effervescent agent.

25. The solid dosage form of claim 13, further comprising at least one disintegration agent; wherein said disintegration agent causes rapid dispersion of said drug-containing emulsion to a target area following oral administration.

26. The solid dosage form of claim 13, further comprising a pH adjusting substance.

27. A method of administering an emulsion composition of claim 1 to a mammal comprising the steps of preparing the emulsion composition and administering the emulsion composition to said mammal.

28. A method is claimed in claim 27 further comprising the step of incorporating said emulsion composition into a solid dosage form, said step of administering said emulsion composition to said mammal including the step of administering the solid dosage form to the mammal.

* * * * *

UNITED STATES PATENT AND TRADEMARK OFFICE
CERTIFICATE OF CORRECTION

PATENT NO. : 6,692,771 B1
DATED : February 17, 2004
INVENTOR(S) : S. Indiran Pather et al.

It is certified that error appears in the above-identified patent and that said Letters Patent is hereby corrected as shown below:

Column 2,
Line 47, "is" should be -- are --.

Column 4,
Line 38, "form a film" should be -- form of a film --.

Column 6,
Line 9, "are" should be -- is --.

Column 10,
Line 27, "emulsion" should be -- emulsions --.

Column 14,
Line 2, "of and" should be -- of any --.

Column 20,
Line 7, "has" should be -- have --.

Column 21,
Example 10, "Satina ITT" should be -- Satina III --.

Column 22,
Line 49, "wherein drug-" should be -- wherein said drug- --.

Column 24,
Line 33, "method is" should be -- method as --.

Signed and Sealed this

Twenty-ninth Day of June, 2004

JON W. DUDAS
*Acting Director of the United States Patent and Trademark Office*